United States Patent
Jensen et al.

(10) Patent No.: US 11,543,375 B2
(45) Date of Patent: Jan. 3, 2023

(54) METHOD, A SYSTEM, AND A PROBE FOR DETERMINING IN-SITU AN OXIDATION-REDUCTION POTENTIAL IN A FORMATION HAVING A SURFACE

(71) Applicant: Ejlskov A/S, Aarhus N (DK)

(72) Inventors: Palle Ejlskov Jensen, Aarhus N (DK); Ivan Yélamos Vela, Aarhus N (DK)

(73) Assignee: Ejlskov A/S, Aarhus N (DK)

( * ) Notice: Subject to any disclaimer, the term of this patent is extended or adjusted under 35 U.S.C. 154(b) by 44 days.

(21) Appl. No.: 17/256,271

(22) PCT Filed: Jun. 28, 2019

(86) PCT No.: PCT/DK2019/050209
§ 371 (c)(1),
(2) Date: Dec. 28, 2020

(87) PCT Pub. No.: WO2020/001722
PCT Pub. Date: Jan. 2, 2020

(65) Prior Publication Data
US 2021/0255127 A1 Aug. 19, 2021

(30) Foreign Application Priority Data
Jun. 29, 2018 (DK) .......................... PA 2018 70451

(51) Int. Cl.
*G01N 27/04* (2006.01)
*G01N 33/24* (2006.01)
*B09C 1/10* (2006.01)

(52) U.S. Cl.
CPC ............. *G01N 27/04* (2013.01); *G01N 33/24* (2013.01); *B09C 1/10* (2013.01); *B09C 2101/00* (2013.01)

(58) Field of Classification Search
CPC .......... G01N 27/04; G01N 33/24; B09C 1/10; B09C 2101/00; G01R 33/00;
(Continued)

(56) References Cited

U.S. PATENT DOCUMENTS 1,913,293 A 6/1933 Schlumberger
2,838,730 A * 6/1958 Lebourg .................. G01V 3/22
324/324

(Continued)

FOREIGN PATENT DOCUMENTS

CA 1188734 A1 6/1985
CA 2146744 A1 10/1996
(Continued)

OTHER PUBLICATIONS

First Office Action and search report issued in counterpart application CN 201980044149 0. Date of Office Action dated Jan. 24, 2022.

*Primary Examiner* — Jermele M Hollington
*Assistant Examiner* — Taqi R Nasir
(74) *Attorney, Agent, or Firm* — Dykema Gossett PLLC

(57) ABSTRACT

Aspects of the present disclosure are directed to a system for determining in-situ oxidation-reduction potential in a formation having a surface separating the formation from an ambient atmosphere. The system may measure the oxidation-reduction potential in-situ, and thereby provide the most precise measurement of the oxidation-reduction potential. The formation surface may be the interface between the ambient atmosphere and the uppermost layer of the formation. The system may comprise a probe for a penetration into the formation. a reference electrode for placing on the formation surface, and a controller configured to communicate with the probe. The controller may be configured to communicate with the reference electrode, determine the oxidation-reduction potential as a potential difference between the reference electrode and the oxidation-reduction electrode, and communicate with the probe, the oxidation-reduction electrode, the reference electrode or any other device by a wire or wireless or a combination of wire and wireless.

17 Claims, 13 Drawing Sheets

(58) Field of Classification Search
CPC ............ G01R 33/0035; G01R 33/0023; G01R 33/0017; G01R 31/3191; G01B 7/004; G01C 17/38; G06F 3/017; G06F 3/0346; G06F 3/012

See application file for complete search history.

(56) References Cited

U.S. PATENT DOCUMENTS

| | | | |
|---|---|---|---|
| 3,098,198 | A | 7/1963 | Salimbeni |
| 3,182,735 | A | 5/1965 | Salimbeni et al. |
| 3,538,425 | A | 11/1970 | Veneziani |
| 3,893,522 | A | 7/1975 | Fertl et al. |
| 4,088,945 | A | 5/1978 | Howell et al. |
| 5,387,869 | A * | 2/1995 | Enomoto ................ G01V 3/06 324/72 |
| 5,798,940 | A | 8/1998 | Bratton |
| 2006/0016763 | A1 | 1/2006 | Kerfoot |
| 2013/0147489 | A1 | 6/2013 | Jackson |
| 2016/0245080 | A1 | 8/2016 | Sun et al. |

FOREIGN PATENT DOCUMENTS

| | | | |
|---|---|---|---|
| CA | 2338668 A1 | 8/2001 | |
| CN | 106802132 A | 6/2017 | |
| CN | 108132286 A | 6/2018 | |
| EP | 0678758 A1 | 10/1995 | |
| EP | 678758 B1 * | 12/1997 | ............. G01V 3/082 |

* cited by examiner

A:

50

B:

76

METHOD, A SYSTEM, AND A PROBE FOR DETERMINING IN-SITU AN OXIDATION-REDUCTION POTENTIAL IN A FORMATION HAVING A SURFACE

CROSS-REFERENCE TO RELATED APPLICATIONS

This application is a national stage filing based upon International PCT Application No. PCT/DK2019/050209, filed 28 Jun. 2019, which claims the benefit of priority to Denmark application No. PA 2018 70451, filed 29 Jun. 2018.

FIELD OF THE INVENTION

The present invention relates to a method, a system, and a probe for determining in-situ an oxidation-reduction potential in a formation having a surface.

The present invention relates to a method, a system, and a probe for determining in-situ a resistivity of a formation having a surface.

BACKGROUND OF THE INVENTION

Agriculture uses fertilisers such as ammonium nitrate for increasing the overall yield. A part of the used fertilisers leach into the surface and may leach further down into the formation, which may have a ground water reservoir. The ground water reservoir becomes in this way contaminated by the fertiliser resulting in ground water, which may not be used as drinking water without extra treatments.

It is very difficult to prevent fertilizer from leaching into the formation and likewise difficult to remove the fertilizer. In some cases, highly contaminated soil has been physically removed, but this is an expensive and labour intensive method. Furthermore, the soil is not cleaned from the fertilizer as the soil is just moved to a less sensitive area.

Naturally occurring bacteria in the surface and the formation may convert nitrate to harmless by-products, however, this is controlled by whether the conditions are anaerobic or aerobic. The denitrifying process is an anaerobic process and the bacteria under anaerobic conditions may convert nitrate to harmless by-products. Thus, surfaces and formations having large parts with anaerobic conditions are more efficient at removing fertilizer and the agriculture may at those fields use more fertilizer with a lesser risk of contaminating ground water. Furthermore, the conversion rate may be increased by adding denitrifying bacteria to the surface and the formation. The denitrifying bacteria must be added to oxygen-depleted parts of the formation as oxygen typically is toxic to the denitrifying bacteria.

The oxidation-reduction potential depends on the amount of oxygen present if there is no oxygen then the oxidation-reduction potential will be negative.

Thus, the oxidation-reduction potential reveals the conditions for the bacteria. The transition from aerobic to anaerobic is called the redox interface. Thus, oxidation-reduction potential measurements are vital for determining the surface and formation nitrate conversion rate. Furthermore the redox interface reveals at which depths the denitrifying bacteria should be added to increase the nitrate conversion rate.

U.S. Pat. No. 5,798,940 patent proposes a single pass ground penetrating probe for in situ measurements of pH and oxidation-reduction potential of soils. The oxidation-reduction potential is determined by determining the potential difference between a reference electrode isolated from the soil by an ion permeable ceramic barrier, and a platinum electrode in direct contact with the soil. The ion permeable ceramic barrier is brittle and may crack if exposed to a too high force or impact. Furthermore, the ceramic barrier delays any changes in potential. The above mentioned problems have led to limited adoption of the ground penetrating probe.

At present, the redox interface is determined based on borehole date, such as water samples, sediment colours or sediment samples. This is however a slow and labour intensive process, which makes it economically less viable.

Experiments have shown that water-bearing layers (e.g. sand) have a different oxidation-reduction potential compared to non-water-bearing layers. Thus, there is a need to determine the lithography of the formation in order to get a complete understanding of the measured oxidation-reduction potential. The lithography of the formation can be analysed by direct current (DC) measurement, but at present day none of the prior art probes and methods are able to determine both the oxidation-reduction potential and the resistivity i.e. lithography of the formation.

Thus, there is a need for a faster and more viable method of determining the characteristics of a formation having a surface, such as the oxidation-reduction potential and/or the resistivity.

Furthermore, there is a need for a system and a probe capable of experiencing high forces and/or pressures while having means for determining the oxidation-reduction potential of the formation and/or the resistivity of the formation.

CN108132286A describes a spear for driving into a surface. The spear having an exposed platinum wire connected to a copper wire being connected to a voltmeter. A reference electrode is placed at the surface of a formation and connected to the voltmeter. The redox-potential is measured as the potential difference between the platinum wire and the reference electrode. The spear is 1 m long and this severely limits the usability of invention as it is not usable for determining the oxidation-reduction potential of formation at depths below 1 m. Furthermore, the spear is pushed by a person into the soil. Thus, the spear cannot solve the above mentioned needs.

OBJECT OF THE INVENTION

It is an object of the invention to provide a method of determining an oxidation-reduction potential in a formation.

It is an object of the invention to provide a system and probe capable of determining an oxidation-reduction potential in a formation.

It is an object of the invention to provide a system and probe capable of determining a resistivity in a formation.

DESCRIPTION OF THE INVENTION

An object of the invention is achieved by a method of determining an oxidation-reduction potential in a formation having a surface.

The method may measure the oxidation-reduction potential in-situ, thereby the method may provide the most precise measurement of the oxidation-reduction potential.

The surface of the formation may be the interface between the ambient atmosphere and the uppermost layer of the formation. In this application the surface is also referred to as the soil.

The method may comprise an act of placing a reference electrode at the surface i.e. in the soil of the formation.

The skilled person would know which reference electrode to use.

The method may comprise an act of penetrating by direct push or rotary drilling or sonic drilling a probe carrying an oxidation-reduction electrode into the formation.

The act of penetrating should be interpreted broadly, as the act of penetrating is equivalent to an act of retracting.

The probe may be a formation penetrating probe.

The oxidation-reduction electrode is capable of experiencing significantly larger forces, compared to the less sturdy reference electrode. The probe only carries the oxidation-reduction electrode, while the reference electrode is external to the probe and placed in the surface of the formation. The positioning of the electrodes enables that the probe can be exposed to larger forces and/or pressures while penetrating, compared to the prior art. Thus, the method is more reliable than the prior art.

Furthermore, because the probe is enabled to experience larger forces and/or pressures, the penetration speed can be increased significantly compared to known probes. The increase in surveying speed decreases the overall costs of surveying the redox interface of an area. At present the average speed of operation is around 70-100 m/day. The speed of operation depends greatly on the geology and depth, but under optimal conditions the speed of operation can be upwards of 150 m/day. Thus, the method enables a larger speed of operation compared to the prior art.

Furthermore, the positioning of the reference electrode at the surface also enables measurements at larger penetration or depths as the pressure may be larger compared to probes carrying both the reference electrode and the oxidation-reduction electrode. Thus, the method may measure the oxidation reduction potential at larger depths such as depths up to 60 m.

Furthermore, the probe can be used in harder formations such as clayed tills with stones and boulders, because the probe is enabled to experience larger forces and/or pressures compared to known probes for determining the oxidation-reduction potential. Thus, the method may, compared to the prior art, be used in geology having a harder formations.

The skilled person would know which drilling technique to use for causing the probe to penetrate the formation.

The drilling technique may be direct push or rotary drilling or sonic drilling.

The method may comprise an act of determining the oxidation-reduction potential as a potential difference between the reference electrode and the oxidation-reduction electrode.

As an example of a determination of an oxidation-reduction potential in a formation having a surface a reference electrode is placed in the surface. This is followed by penetrating a probe carrying an oxidation-reduction electrode into the formation. In a last act the oxidation-reduction potential is determined as the potential difference between the reference electrode and the oxidation-reduction electrode.

As another example of a determination of an oxidation-reduction potential in a formation having a surface a reference electrode is placed in the surface. This is followed by retracting a probe carrying an oxidation-reduction electrode from the formation. In a last act, the oxidation-reduction potential is determined as the potential difference between the reference electrode and the oxidation-reduction electrode.

In an aspect, the act of determining the oxidation-reduction potential may be performed whilst penetrating.

Thus, the oxidation-reduction potential may be determined in-situ and in real time, which enables an easier determination of the redox-interface as the method provides data continuously. If the user is only searching for the first redox-interface, then the user stop the act of penetrating when the redox-interface has been found. The user may afterwards retract the probe and move the equipment to the next positioning and reiterate. This increases the speed of mapping or surveying of areas by a large factor.

Furthermore, since the act of determining the oxidation-reduction potential is performed on-site and in-situ a user is enabled to recognise corrupted or bad data and reiterate the method anew. Thereby, the overall quality of data may be increased.

In an aspect, the act of penetrating may be performed by directing the probe as a function of time.

In certain cases the probe is penetrating into the soil continuously without any breaks, and in these cases time measurements are good for evaluating data.

If the probe is penetrating at a constant or at a near constant speed, the time may be converted to penetration or a level of penetration or a depth.

Furthermore, by performing the act of penetrating as a function of time, the operation is simplified as a simple timer is needed. This simplification is inexpensive but may still be used to determine the present of the redox interface with a sufficient precession.

In an aspect, the act of penetrating involves an act of establishing a penetration of the probe into the formation; and wherein the act of determining the oxidation-reduction potential may be performed as a function of the penetration.

The penetration may be established by using a string potentiometer, which may have a resolution of +/−0.5 cm.

Penetration is to be understood as the level of penetration or as a depth. In some cases the probe is penetrating straight down and in these cases the penetration is equal to the depth of the probe. In other cases the probe is penetrating with an angle, compared to the surface or the probe changes direction while penetrating and in these cases, a level of penetration is established.

In all cases the determination of the oxidation-reduction potential as a function of the penetration will enable a user to determine the redox interface with greater precision.

Thereby, the user will be able to determine at which depths denitrification bacteria should be added.

The act of establishing a penetration is possible using direct push (hammering/percussion), sonic or cone penetrometer test (CPT) with static pressure.

In an aspect, the method may further comprise an act of retracting the probe from the formation and performing a direct current (DC) measurement during retraction.

The probe may further comprise a meter comprising two resistivity electrodes for measuring a voltage difference and, thereby, determining a resistivity of the formation. The two resistivity electrodes are positioned at a mutual distance on the probe. The meter may further comprise two current electrodes for providing a direct current to the formation. The two current electrodes may be placed on each side of the probe at the surface.

In another embodiment the probe may further comprise a meter comprising two resistivity electrodes for measuring a voltage difference and two current electrodes for providing a current to the formation. The four electrodes are positioned along the probe where the two current electrodes encompass the two resistivity electrodes.

The electrodes may be placed such that each electrode has equal distance to neighbouring electrodes, as this will provide a better resistivity measurement.

The two current electrodes may be ring electrodes.

The two resistivity electrodes may be ring electrodes.

The current and resistivity electrodes may be ring electrodes and they may be in a Wenner configuration along the probe. Experiments have shown that this configuration gives the best measurements and thus, the best values for the resistivity of the formation.

The resistivity measurement will improve the interpretation of the oxidation-reduction potential, because water-bearing layers (e.g. sand) have been shown to have a different oxidation-reduction potential, compared to non-water-bearing layers. The resistivity measurement gives information of the lithography of the formation and thus, the direct current (DC) measurement during retraction complements the oxidation-reduction potential as it is needed for properly interpreting the oxidation-reduction potential.

By having all electrodes on the probe, the method is simplified as there is no need to inserting the current electrodes in the surface of the formation. Furthermore, the measurement is more localized which will increase the resolution of the measurement.

Thus, the method may determine the oxidation-reduction potential during the act of penetration and the method may determine the resistivity of the formation during retraction.

Both the oxidation-reduction potential and the resistivity of the formation may be determined as a function of the penetration.

The precision of the measurement of the penetration or depth is greatest during penetration, compared to retraction due to a mechanical drift of the equipment when retracting. Thus, the most important measurement should be performed during penetration and the least important measurement should be performed during retraction.

In an embodiment of the method, the direct current (DC) measurement may be performed during penetration and the oxidation-reduction potential may be determined during retraction. In this case the resistivity will have a better penetration resolution.

The method may use direct push as the combination of direct push and a DC measurement setup using four ring electrodes along the probe in a Wenner configuration have been shown to be particularly good at determining the resistivity, while being able to penetrate at a high speed.

An object of the invention is achieved by a system for determining in-situ oxidation-reduction potential in a formation having a surface separating the formation from an ambient atmosphere.

The system may measure the oxidation-reduction potential in-situ, thereby the system may provide the most precise measurement of the oxidation-reduction potential. Furthermore cost is lower compared to making a borehole and analysing the borehole data.

The surface of the formation may be the interface between the ambient atmosphere and the uppermost layer of the formation. In this application the surface may also referred to as the soil.

The system may comprise a probe for a penetration into the formation. The probe may comprise an oxidation-reduction electrode.

The probe may be a ground penetrating probe.

The system may comprise a reference electrode for placing on the surface of the formation. The reference electrode may be external to the probe and the reference electrode may have a pointed end for properly inserting the reference electrode into the surface of the formation.

The pointed end will stabilise the reference electrode during the penetration of the probe into the formation.

The skilled person would know which reference electrode to use.

The reference electrode may be a silver chloride reference electrode.

The probe may not comprise the reference electrode.

The oxidation-reduction electrode is capable of experiencing significantly larger forces, compared to the less sturdy reference electrode. The probe only carries the oxidation-reduction electrode, while the reference electrode is external to the probe and placed in the surface of the formation. The positioning of the electrodes enables that the probe can be exposed to larger forces and/or pressures while penetrating, compared to the prior art.

Furthermore, because the probe is enabled to experience larger forces and/or pressures, the penetration speed can be increased significantly compared to known probes. The increase in surveying speed decreases the overall costs of surveying the redox interface of an area. At present the average speed of operation is around 70-100 m/day. The speed of operation depends greatly on the geology and depth, but under optimal conditions the speed of operation can be upwards of 150 m/day.

Furthermore, the positioning of the reference electrode at the surface also enables measurements at larger penetration or depths as the pressure may be larger compared to probes carrying both the reference electrode and the oxidation-reduction electrode.

Furthermore, the probe can be used in harder formations such as clayed tills with stones and boulders, because the probe is enabled to experience larger forces and/or pressures compared to known probes for determining the oxidation-reduction potential.

The system may comprise a controller, which may be configured to communicate with the probe.

The controller may be configured to communicate with the reference electrode.

The controller may further be configured to determine the oxidation-reduction potential as a potential difference between the reference electrode and the oxidation-reduction electrode.

The controller may communicate with the probe, the oxidation-reduction electrode, the reference electrode or any other device by a wire or wireless or a combination of wire and wireless.

The oxidation-reduction electrode may be a metal electrode as it is able to withstand large forces or pressures.

The oxidation-reduction electrode may be a noble metal electrode as it is able to withstand large forces or pressures and noble metals are chemically inert, thereby decreasing drift caused by chemical reaction.

The oxidation-reduction electrode may be a platinum electrode as it is well known and have excellent characteristics.

The skilled person would know which drilling technique to use for causing the probe to penetrate the formation. The drilling technique may be direct push or rotary drilling or sonic drilling.

In an aspect, the system may further comprise a penetrometer in communication with the controller, which may further be configured to determine the oxidation-reduction potential as a function of the penetration into the formation.

The penetrometer may be a string potentiometer which is an easy and reliable tool for measuring a position and/or velocity.

The skilled person should understand penetration as the level of penetration or as a depth. In some cases the probe is penetrating straight down and in these cases the penetration is equal to the depth of the probe. In other cases the probe is penetrating with an angle compared to the surface or the probe changes direction while penetrating and in these cases a level of penetration is established.

The penetrometer enables a very precise penetration determination i.e. +/−0.5 cm. Thereby the system may provide excellent data for determining the precise redox interface or for determining the resistivity of the formation.

In an aspect, the system may further comprise a timer in communication with the controller. The controller may further be configured to determine the oxidation-reduction potential as a function of time.

In certain cases the probe is penetrating into the soil continuously without any breaks, and in these cases time is good for evaluating data.

If the probe is penetrating at a constant or at a near constant speed, the time may be converted to penetration or a level of penetration or a depth.

Furthermore, by performing the act of penetrating as a function of time, the operation is simplified as a simple timer is needed. This simplification is inexpensive but may still be used to determine the present of the redox interface with a sufficient precession.

In an aspect, the system may further comprise a meter, which meter is configured for measuring a direct current (DC). The controller may be further configured to determine the resistivity as a function of time, penetration, or both time and penetration.

The probe may further comprise a meter comprising two resistivity electrodes for measuring a voltage difference and, thereby, determining a resistivity of the formation. The two resistivity electrodes are positioned at a mutual distance on the probe. The meter may further comprise two current electrodes for providing a direct current to the formation. The two current electrodes may be placed on each side of the probe at the surface.

In another embodiment the probe may further comprise a meter comprising two resistivity electrodes for measuring a voltage difference and two current electrodes for providing a current to the formation. The four electrodes are positioned along the probe where the two current electrodes encompass the two resistivity electrodes.

The electrodes may be placed such that each electrode has equal distance to neighbouring electrodes as this will provide a better resistivity measurement.

The two current electrodes may be ring electrodes.

The two resistivity electrodes may be ring electrodes.

The current and resistivity electrodes may be ring electrodes and they may be in a Wenner configuration along the probe. Experiments have shown that this configuration gives the best measurements and thus the best values for the resistivity of the formation.

The resistivity measurement will improve the interpretation of the oxidation-reduction potential, because water-bearing layers (e.g. sand) have been shown to have a different oxidation-reduction potential compared to non-water-bearing layers. The resistivity measurement gives information of the lithography of the formation and thus the direct current (DC) measurement during retraction complements the oxidation-reduction potential as it is needed for properly interpreting the oxidation-reduction potential.

By having all electrodes on the probe, the method is simplified as there is no need to inserting the current electrodes in the surface of the formation. Furthermore, the measurement is more localized which will increase the resolution of the measurement.

The system may use direct push as the combination of direct push and a DC measurement setup using four ring electrodes along the probe in a Wenner configuration have been shown to be particularly good at determining the resistivity, while being able to penetrate at a high speed.

In an aspect, the oxidation-reduction electrode may be a metal electrode substantially encapsulated in and galvanically isolated from a probe body of the probe.

By encapsulating and galvanically isolating the oxidation-reduction electrode, the risk of drift of the potential is minimised considerably as the oxidation-reduction electrode is electrically in contact with the formation while being isolated from the probe body.

The oxidation-reduction electrode may be a noble metal. The noble metal is chemically stable and the measured potential will not drift with time due to reactions and the noble metals are capable of withstanding high forces and pressures.

The oxidation-reduction electrode may be platinum as it is known to have optimal characteristics.

In an aspect, the oxidation-reduction electrode may comprise an electrode body encapsulating the metal electrode and the electrode body may be an insulator for galvanically isolating the metal electrode.

The electrode body may be made of composite material or plastic, which is capable of withstanding high forces or pressures without deteriorating or deformation, while being able to isolate the metal electrode from the probe.

The electrode body may comprise a protrusion complementary to a through going recess in the probe body. The connection between the probe body and the electrode body must be tight and mechanically stable even at large forces or pressures such that the potential measured does not drift with time. This will also enable the probe to penetrate with a larger penetration speed as the oxidation-reduction electrode will be able to handle larger forces or pressures.

The protrusion may have an outer face with an exposed part of the metal electrode, such that the metal electrode is in direct contact with the formation when the probe is in intended use.

The outer face and the probe body may together form a flush surface.

In an embodiment the system may further comprise an oxidation-reduction electrode holder for mechanically stabilising the oxidation-reduction electrode.

The oxidation-reduction electrode holder may be inserted into the central part of the probe body, such that the oxidation-reduction electrode holder pushes the oxidation-reduction electrode towards the internal side of the probe body.

The oxidation-reduction electrode holder may have a slit towards a central recess for engaging with the metal electrode of the oxidation-reduction electrode.

In an aspect, the oxidation-reduction electrode may be encapsulated by an electrode body, wherein the electrode body may comprise a protrusion complementary to a through going recess in the probe body. The protrusion may have an outer face with an exposed part of the oxidation-reduction electrode.

The electrode body may be made of composite material or plastic, which is capable of withstanding high forces or pressures without deteriorating or deformation, while being able to isolate the metal electrode from the probe.

The connection between the probe body and the electrode body must be tight and mechanically stable even at large forces or pressures such that the potential measured does not drift with time. This will also enable the probe to penetrate with a larger penetration speed as the oxidation-reduction electrode will be able to handle larger forces or pressures.

The protrusion may have an outer face with an exposed part of the oxidation-reduction electrode, such that the electrode is in direct contact with the formation when the probe is in intended use.

The outer face and the probe body may together form a flush surface.

An object of the invention is achieved by a computer program product comprising instructions on a computer to cause the system to perform the method of determining the oxidation-reduction potential.

An object of the invention is achieved by a computer-readable medium having stored thereon the computer program.

An object of the invention is achieved by a probe for a penetration into a formation. The probe may comprise a probe body. The probe body may have a probe front for a penetration of the formation.

The probe body may further be supporting an oxidation-reduction electrode.

The probe may be a formation penetrating probe.

The probe does not comprise a reference electrode as the reference electrode. The oxidation-reduction electrode is capable of experiencing significantly larger forces, compared to the less sturdy reference electrode. Thus, when the probe only carries the oxidation-reduction electrode, while the reference electrode is external to the probe, then the probe can be exposed to larger forces and/or pressures while penetrating, compared to the prior art.

Furthermore, because the probe is enabled to experience larger forces and/or pressures, the penetration speed can be increased significantly compared to known probes. The increase in surveying speed decreases the overall costs of surveying the redox interface of an area. At present the average speed of operation is around 70-100 m/day. The speed of operation depends greatly on the geology and depth, but under optimal conditions the speed of operation can be upwards of 150 m/day.

Furthermore, the positioning of the reference electrode at the surface also enables measurements at larger penetration or depths as the pressure may be larger compared to probes carrying both the reference electrode and the oxidation-reduction electrode.

Furthermore, the probe can be used in harder formations such as clayed tills with stones and boulders, because the probe is enabled to experience larger forces and/or pressures compared to known probes for determining the oxidation-reduction potential.

In an aspect, the oxidation-reduction electrode may be a metal electrode as it is able to withstand large forces or pressures.

In an aspect, the oxidation-reduction electrode may be a noble metal electrode as it is able to withstand large forces or pressures and noble metals are chemically inert, thereby decreasing drift caused by chemical reaction.

The oxidation-reduction electrode may be a platinum electrode as it is well known and have excellent characteristics.

In an aspect, the oxidation-reduction electrode may be a metal electrode, substantially encapsulated in and galvanically isolated from the probe body.

By encapsulating and galvanically isolating the oxidation-reduction electrode the risk of drift of the potential is minimised considerably as the oxidation-reduction electrode is electrically in contact with the formation while being isolated from the probe body.

In an aspect, the oxidation-reduction electrode may be a noble metal electrode substantially encapsulated in and galvanically isolated from the probe body.

By encapsulating and galvanically isolating the oxidation-reduction electrode, the risk of drift of the potential is minimised considerably as the oxidation-reduction electrode is electrically in contact with the formation while being isolated from the probe body.

The oxidation-reduction electrode may be a platinum electrode as it is well known and have excellent characteristics.

In an aspect, the oxidation-reduction electrode may comprise an electrode body encapsulating the metal electrode and the electrode body may be an insulator for galvanically isolating the metal electrode.

The electrode body may be made of composite material or plastic, which is capable of withstanding high forces or pressures without deteriorating or deformation, while being able to isolate the metal electrode from the probe.

The electrode body may comprise a protrusion complementary to a through going recess in a probe body. The connection between the probe body and the electrode body must be tight and mechanically stable, even at large forces or pressures, such that the potential measures does not drift with time. This will also enable the probe to penetrate with a larger penetration speed as the oxidation-reduction electrode will be able to handle larger forces or pressures.

The protrusion may have an outer face with an exposed part of the metal electrode, such that the metal electrode is in direct contact with the formation when the probe is in intended use.

In an aspect, the oxidation-reduction electrode may be encapsulated by an electrode body, wherein the electrode body may comprise a protrusion complementary to a through going recess in the probe body. The protrusion may have an outer face with an exposed part of the oxidation-reduction electrode.

DESCRIPTION OF THE DRAWING

Embodiments of the invention will be described in the figures, whereon.

DETAILED DESCRIPTION OF THE INVENTION

| Item | No |
|---|---|
| Formation | 10 |
| Surface | 12 |
| Ambient atmosphere | 16 |
| Redox interface | 18 |
| System | 20 |
| Controller | 30 |
| Communication | 32 |
| Probe | 40 |
| Probe body | 42 |
| Probe front | 44 |
| Oxidation-reduction potential | 50 |
| Reference electrode | 52 |
| Oxidation-reduction electrode | 54 |
| Electrode body | 55 |
| Oxidation-reduction electrode holder | 56 |
| Protrusion | 58 |
| Outer face | 59 |
| Penetrometer | 60 |
| Penetration | 62 |
| Meter | 70 |
| Resistivity electrode | 72 |
| Current electrode | 74 |
| Resistivity | 76 |
| Plastic ring | 80 |
| Plastic tube | 82 |
| Method | 1000 |
| Placing | 1100 |
| Penetrating | 1200 |
| Retracting | 1300 |
| Determining | 1400 |
| Establishing | 1500 |

Figure 1:
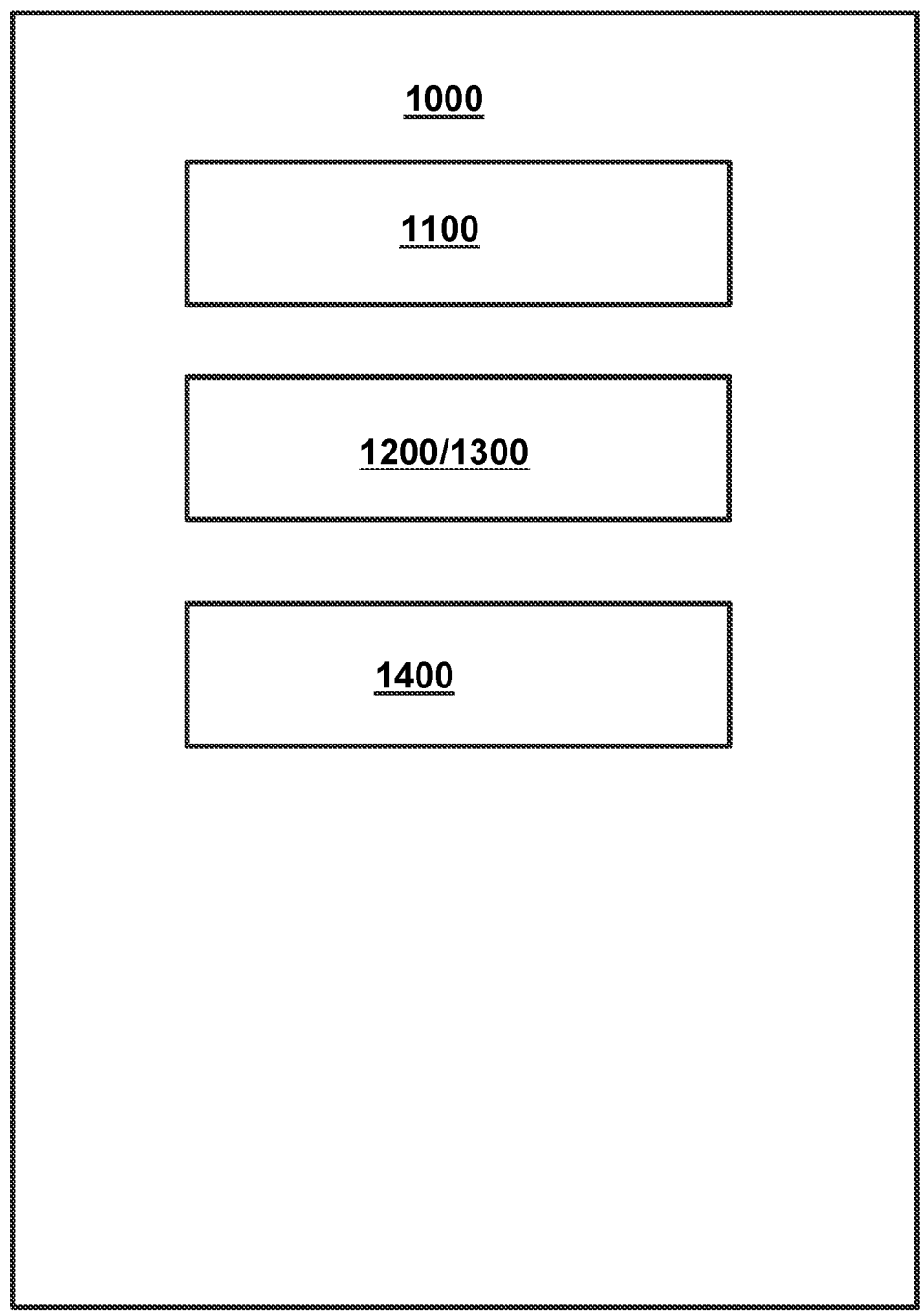
FIG. 1 illustrates a method of determining an oxidation-reduction potential [in situ] in a formation.

FIG. 1 illustrates a method 1000 of determining an oxidation-reduction potential 50 in a formation 10 having a surface 12.

The method 1000 comprises the act of placing 1100 a reference electrode 52 at the surface 12. There is a further act of penetrating 1200 or retracting 1300 a probe 40 carrying an oxidation-reduction electrode 54 into the formation 10. There is a further act of determining 1400 the oxidation-reduction potential 50 as the potential difference between the reference electrode 52 and the oxidation-reduction electrode 54.

As an example, the reference electrode 52 is placed at the surface of the formation 10. Afterwards a drilling mechanism will perform the act of penetrating 1200 the probe 40 into the formation 10. The probe 40 carries an oxidation-reduction electrode 54. A controller 30, being in wireless or wired communication 32 with the oxidation-reduction electrode 54 and the reference electrode 52, will perform the act of determining 1400 the oxidation-reduction potential 50 as the potential difference between the reference electrode 52 and the oxidation-reduction electrode 54.

Figure 3:
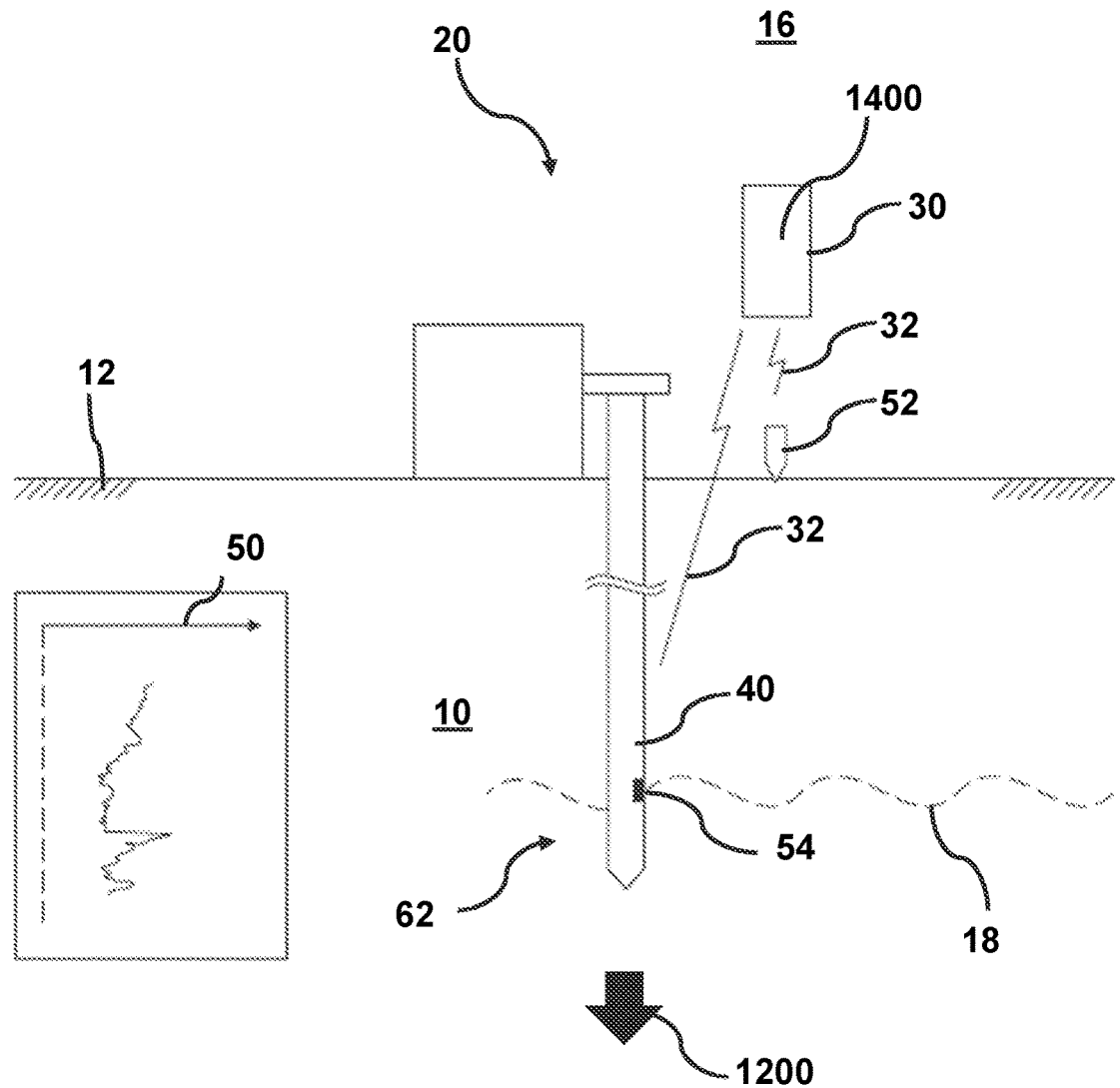
FIG. 3 illustrates a system for determining in-situ oxidation-reduction potential in a formation.
Figure 4:
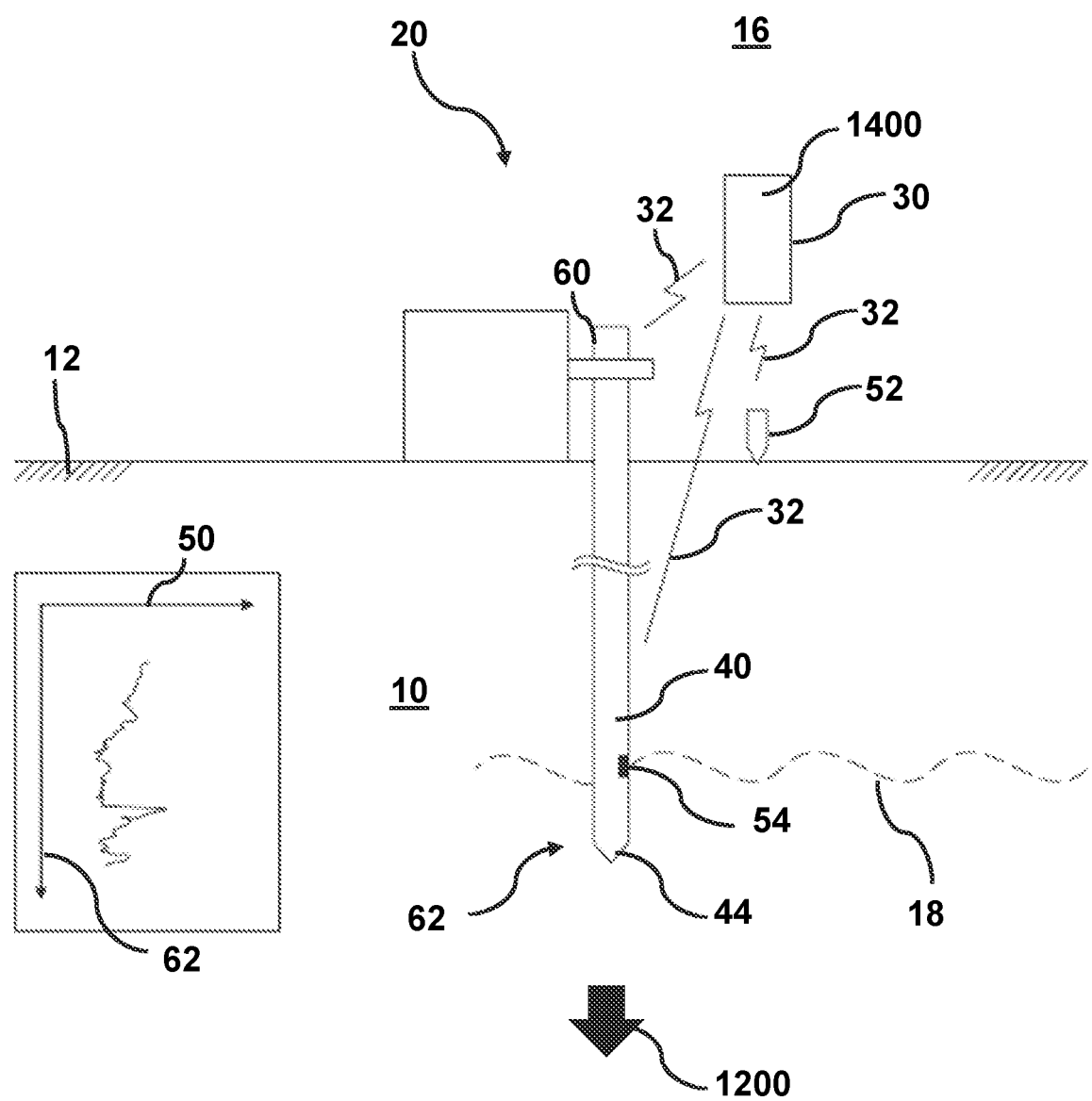
FIG. 4 illustrates a system for determining in-situ oxidation-reduction potential in a formation as a function of penetration.
Figure 9:
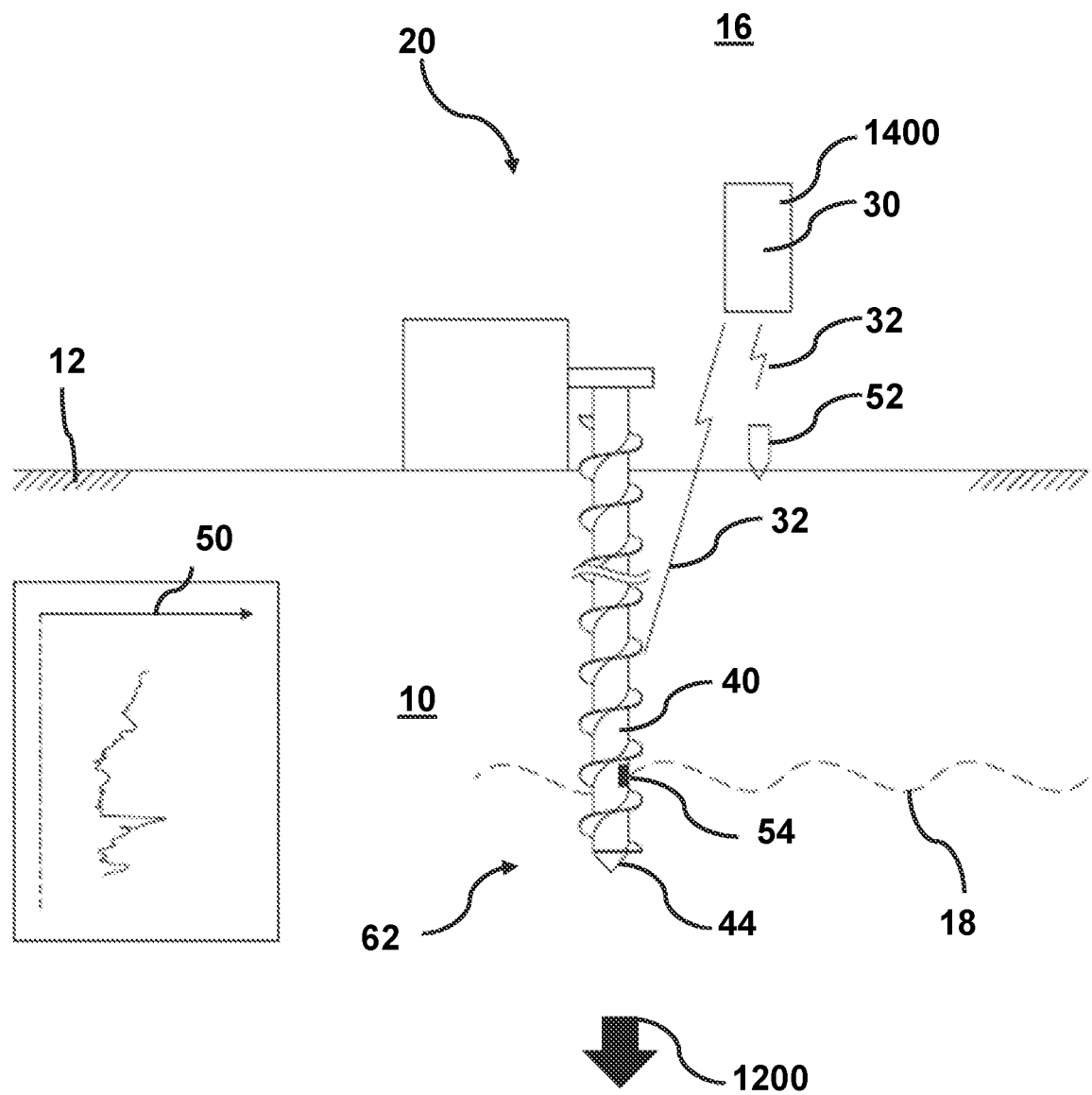
FIG. 9 illustrates a system for determining in-situ oxidation-reduction potential in a formation using a probe having an auger.

In FIGS. 3, 4 and 9 a system 20 has executed the above mentioned method 1000, wherein the act of determining 1400 the oxidation-reduction potential 50 is performed whilst penetrating 1200.

Figure 2:
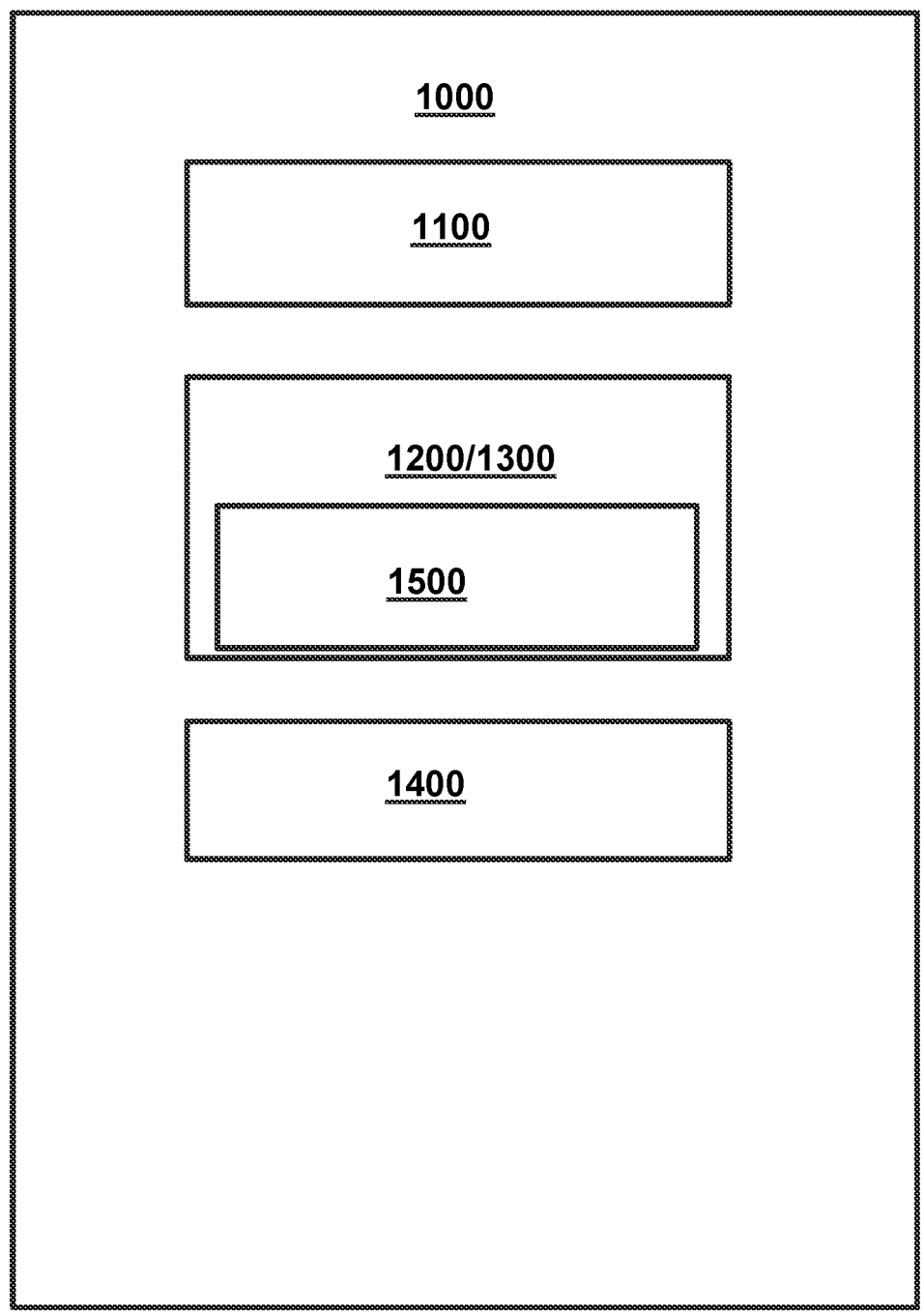
FIG. 2 illustrates a determined oxidation-reduction potential as a function of penetration.

FIG. 2 illustrates a determined oxidation-reduction potential 50 as a function of penetration 62.

The method 1000 comprises an act of placing 1100 a reference electrode 52 at the surface 12. There is a further act of penetrating 1200 or retracting 1300 a probe 40 carrying an oxidation-reduction electrode 54 into the formation 10. Wherein the act of penetrating 1400 or retracting 1300 involves an act of establishing 1500 a penetration 62 of the probe 40 into the formation 10; and wherein the act of determining 1400 the oxidation-reduction potential 50 is performed as a function of the penetration 62.

As an example, the reference electrode 52 is placed at the surface of the formation 10. Afterwards, a drilling mechanism will perform the act of penetrating 1200 the probe 40 into the formation 10. The probe 40 carries an oxidation-reduction electrode 54. A penetrometer 60 for measuring a penetration 62 of the probe is in connection with the probe 40. A controller 30, which is in wireless or wired communication 32 with the oxidation-reduction electrode 54, the reference electrode 52, will perform the act of determining 1400 the oxidation-reduction potential 50 as the potential difference between the reference electrode 52 and the oxidation-reduction electrode 54. The controller 30 is also in wireless or wired communication 32 with the penetrometer 60 and the oxidation-reduction potential 50 as a function of the penetration 62 into the formation 10 is therefore determined.

In FIG. 4 a system 20 has executed the above mentioned method 1000, wherein the act of determining 1400 the oxidation-reduction potential 50 as a function of the penetration 62 into the formation 10 is performed whilst penetrating 1200.

FIG. 3 illustrates a system 20 for determining in-situ oxidation-reduction potential 50 in a formation 10. The formation 10 has a surface 12 which separates the formation 10 from the ambient atmosphere 16.

The system 20 comprises a probe 40 for penetration 62 into the formation 10. The probe comprises an oxidation-reduction electrode 54. The oxidation-reduction electrode 54 may be a metal electrode or noble metal electrode or a platinum electrode.

The system can comprise any drilling mechanism and the drilling mechanism is therefore disclosed as a rectangle next to the probe 40.

The system 20 further comprises external to the probe 40 a reference electrode 52. The reference electrode 52 is placed at the surface 12 of the formation 10.

The system 20 further comprises a controller 30, which is configured to communicate 32 by wire or wirelessly with:
the probe 40; and
the reference electrode 52.

The controller 30 is further configured to perform an act of determining 1400 the oxidation-reduction potential 50 as a potential difference between the reference electrode 52 and the oxidation-reduction electrode 54.

The arrow below the probe 40 indicates the movement of the probe 40 and in this figure, the probe 40 is penetrating 1200 the formation 10.

The oxidation-reduction electrode 54 is crossing a dashed line in the figure, which indicates the redox interface 18.

A sketch of graph is disclosed, where the first axis has arbitrary units and the second axis is the determined oxidation-reduction potential 50 and the redox interface 18 is indicated by a large change in potential.

FIG. 4 illustrates a system 20 for determining in-situ oxidation-reduction potential 50 in a formation as a function of penetration 62. The formation 10 has a surface 12 which separates the formation 10 from the ambient atmosphere 16.

The system 20 comprises a probe 40 for a penetration 62 into the formation 10. The probe comprises an oxidation-reduction electrode 54.

The system can comprise any drilling mechanism and the drilling mechanism is therefore disclosed as a rectangle next to the probe 40.

The system 20 further comprises external to the probe 40 a reference electrode 52.

The reference electrode 52 is placed at the surface 12 of the formation 10.

The system 20 further comprises a penetrometer 60 for determining a penetration 62 of the probe 40.

The penetrometer 60 is a string potentiometer.

The system 20 comprises a controller 30 which is configured to communicate 32 by wire or wirelessly with
The probe 40;
The reference electrode 52; and
The penetrometer 60.

The controller 30 is further configured to determining 1400 the oxidation-reduction potential 50 as a potential difference between the reference electrode 52 and the oxidation-reduction electrode 54 as a function of the penetration 62 into the formation 10.

The arrow below the probe 40 indicates the movement of the probe 40 and in this figure, the probe 40 is penetrating 1200 the formation 10.

The oxidation-reduction electrode 54 is crossing a dashed line in the figure which indicates the redox interface 18.

A sketch of graph is disclosed, where the first axis is the penetration 62 and the second axis is the determined oxidation-reduction potential 50 and the redox interface 18 is indicated by a large change in potential.

Figure 5:
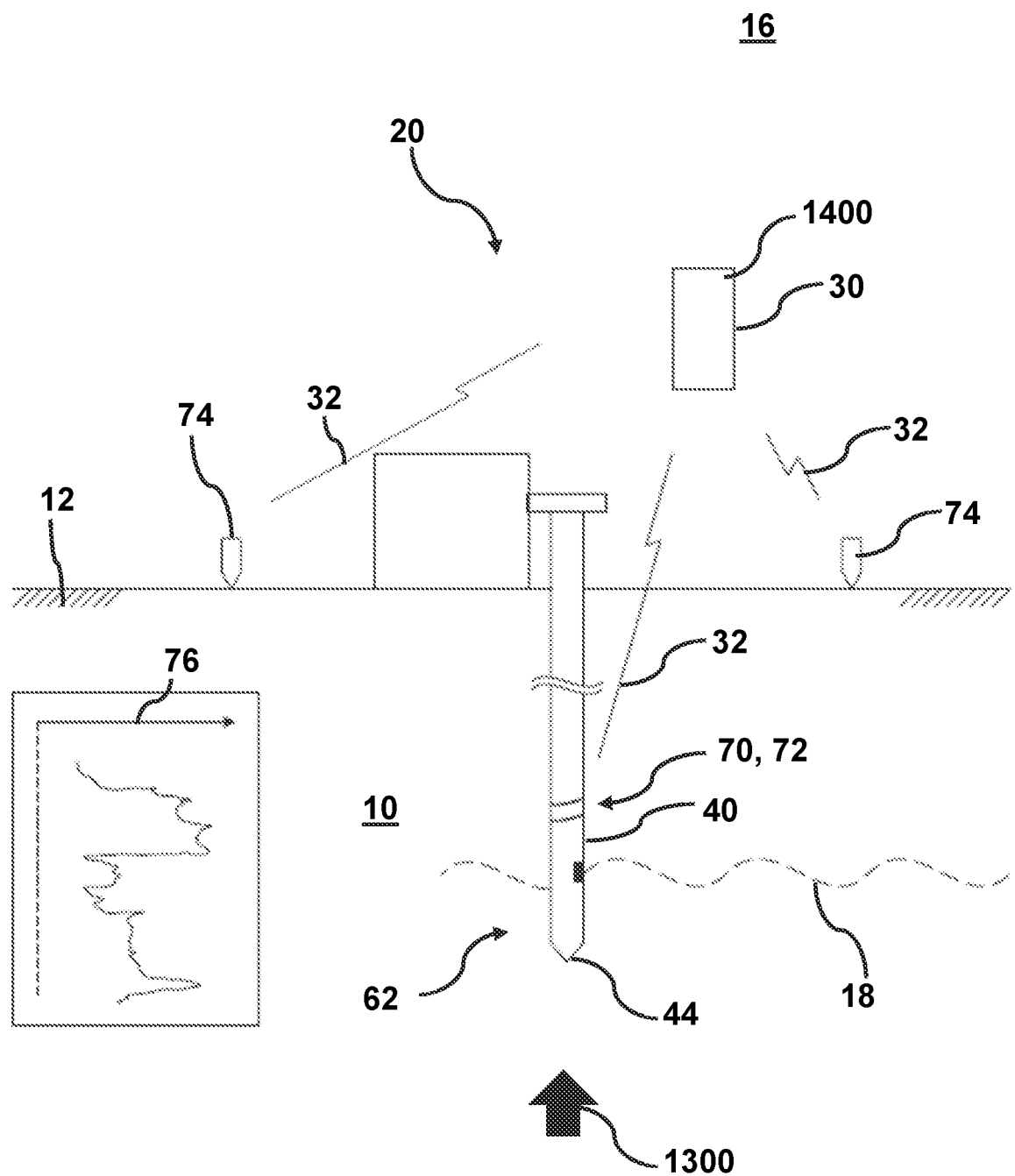
FIG. 5 illustrates a system for determining in-situ resistivity in a formation.

FIG. 5 illustrates a system 20 for determining in-situ resistivity 76 in a formation 20. The formation 10 has a surface 12 separating the formation 10 from the ambient atmosphere 16.

The system 20 comprises a probe 40 for penetration 62 into the formation 10. The probe comprises a meter 70 having two resistivity electrodes 72 for measuring a potential/measuring a direct current (DC).

The system can comprise any drilling mechanism, and the drilling mechanism is therefore disclosed as a rectangle next to the probe 40.

The system 20 further comprises a pair of current electrodes 74, 74 for providing a direct current. The current electrodes 74, 74 are placed at the surface 12 of the formation 10.

The system 20 further comprises a controller 30, which is configured to communicate 32 by wire or wirelessly with:
The probe 40 with the meter 70; and
The pair of current electrodes 74, 74.

The controller 30 is configured to determine the resistivity 76 of the formation, based on applied direct current and potential between the resistivity electrodes 72.

The pair of current electrodes 74, 74 is positioned on each side of the probe 40.

The arrow below the probe 40 indicates the movement of the probe 40 and in this figure, the probe 40 is retracting 1300 from the formation 10.

A dashed line in the figure indicates the redox interface 18.

A sketch of graph is disclosed, where the first axis is in arbitrary units and the second axis is the determined resistivity 76.

Figure 6:
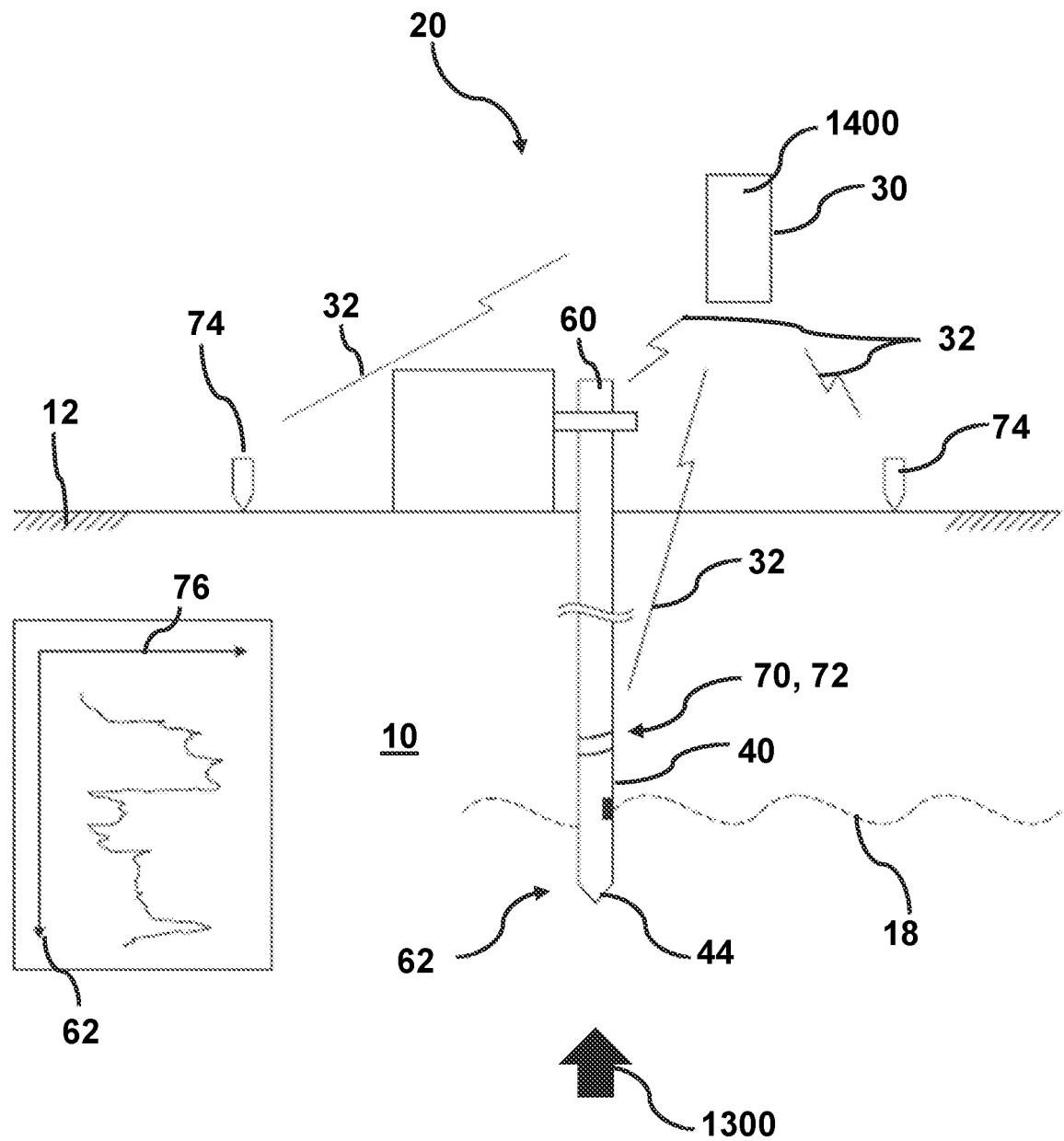
FIG. 6 illustrates a system for determining in-situ resistivity in a formation as a function of penetration.

FIG. 6 illustrates a system 20 for determining in-situ resistivity 76 in a formation 10 as a function of penetration 62. The formation 10 has a surface 12 separating the formation 10 from the ambient atmosphere 16.

The system 20 comprises a probe 40 for a penetration 62 into the formation 10. The probe comprises a meter 70, having two resistivity electrodes 72 for measuring a potential/measuring a direct current (DC).

The system can comprise any drilling mechanism and the drilling mechanism is therefore disclosed as a rectangle next to the probe 40.

The system 20 further comprises a pair of current electrodes 74, 74 for providing a direct current. The current electrodes 74, 74 are placed at the surface 12 of the formation 10.

The system 20 further comprises a penetrometer 60 for determining a penetration 62 of the probe 40.

The penetrometer 60 is a string potentiometer.

The system 20 further comprises a controller 30 which is configured to communicate 32 by wire or wirelessly with:
The probe 40 with the meter 70;
The pair of current electrodes 74, 74; and
The penetrometer 60.

The controller 30 is further configured to determine the resistivity 76 of the formation based on applied direct current and potential between the resistivity electrodes 72 as a function of penetration 62.

The pair of current electrodes 74, 74 is positioned on each side of the probe 40.

The arrow below the probe 40 indicates the movement of the probe 40 and in this figure, the probe 40 is retracting 1300 from the formation 10.

A dashed line in the figure indicates the redox interface 18.

A sketch of graph is disclosed, where the first axis is the penetration 62 in arbitrary units and the second axis is the determined resistivity 76.

Figure 7:
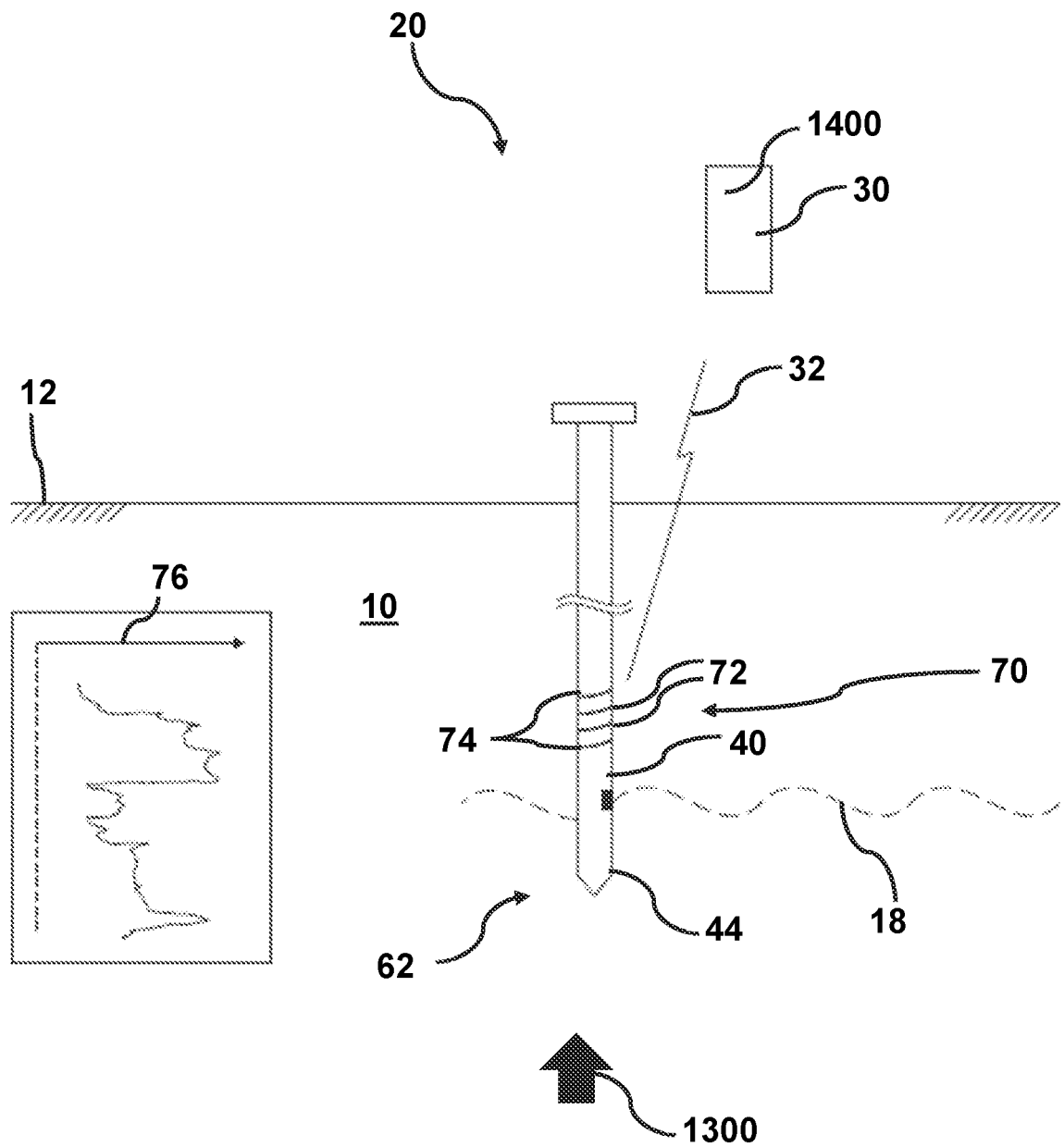
FIG. 7 illustrates a system with a Wenner configuration for determining in-situ resistivity in a formation.

FIG. 7 illustrates a system 20 with a Wenner configuration for determining in-situ resistivity 76 in a formation 10.

The formation 10 has a surface 12 separating the formation 10 from the ambient atmosphere 16.

The system 20 comprises a probe 40 for penetration 62 into the formation 10. The probe comprises a meter 70 having two resistivity electrodes 72 for measuring a potential/measuring a direct current (DC) and two current electrodes 74 for providing a direct current.

The electrodes 72, 74 of the meter are in a Wenner configuration and the electrodes 72, 74 are ring electrodes.

The system can comprise any drilling mechanism, and the drilling mechanism is therefore disclosed as a rectangle next to the probe 40.

The system 20 further comprises a controller 30, which is configured to communicate 32 by wire or wirelessly with the probe 40 with the meter 70.

The controller 30 is configured to determine the resistivity 76 of the formation, based on applied direct current and potential between the resistivity electrodes 72.

The arrow below the probe 40 indicates the movement of the probe 40 and in this figure, the probe 40 is retracting 1300 from the formation 10.

A dashed line in the figure indicates the redox interface 18.

A sketch of graph is disclosed, where the first axis is in arbitrary units and the second axis is the determined resistivity 76.

Figure 8:
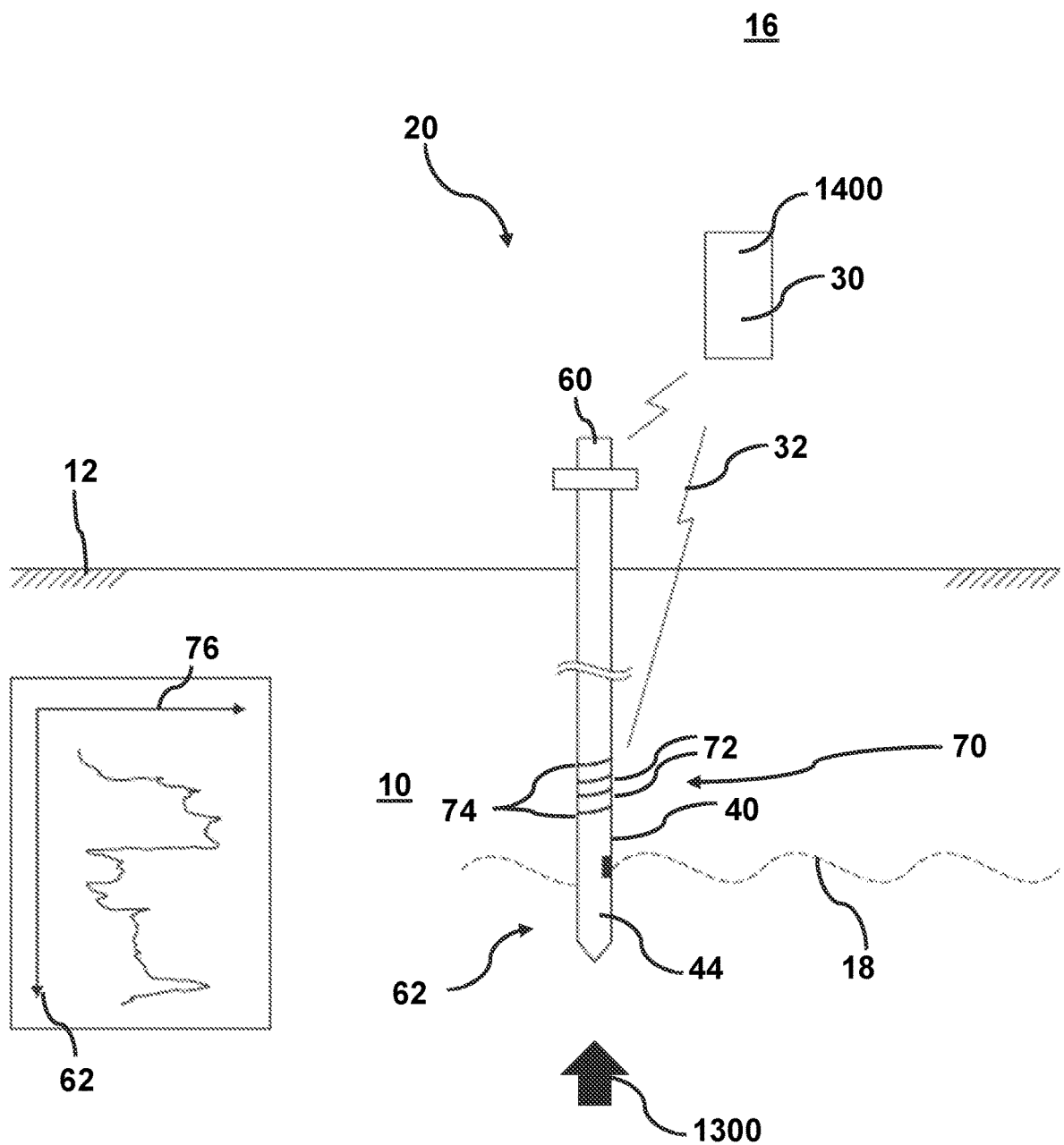
FIG. 8 illustrates a system with a Wenner configuration for determining in-situ resistivity in a formation as a function of penetration.

FIG. 8 illustrates a system 20 with a Wenner configuration for determining in-situ resistivity 76 in a formation 12 as a function of penetration 62.

The formation 10 has a surface 12 separating the formation 10 from the ambient atmosphere 16.

The system 20 comprises a probe 40 for penetration 62 into the formation 10. The probe comprises a meter 70 having two resistivity electrodes 72 for measuring a potential/measuring a direct current (DC) and two current electrodes 74 for providing a direct current.

The electrodes 72, 74 of the meter are in a Wenner configuration and the electrodes 72, 74 are ring electrodes.

The system can comprise any drilling mechanism and the drilling mechanism is therefore disclosed as a rectangle next to the probe 40.

The system 20 further comprises a penetrometer 60 for determining a penetration 62 of the probe 40.

The penetrometer 60 is a string potentiometer.

The system 20 further comprises a controller 30 which is configured to communicate 32 by wire or wirelessly with:

The probe 40 with the meter 70; and
The penetrometer 60.

The controller 30 is further configured to determine the resistivity 76 of the formation based on applied direct current and potential between the resistivity electrodes 72 as a function of penetration 62.

The arrow below the probe 40 indicates the movement of the probe 40 and in this figure, the probe 40 is retracting 1300 from the formation 10.

A dashed line in the figure indicates the redox interface 18.

A sketch of graph is disclosed, where the first axis is the penetration 62 in arbitrary units and the second axis is the determined resistivity 76.

FIG. 9 illustrates a system 20 for determining in-situ oxidation-reduction potential 50 in a formation 10 using a probe 40 having an auger. FIG. 7 only differs from FIG. 3 by the probe having an auger.

Figure 10:
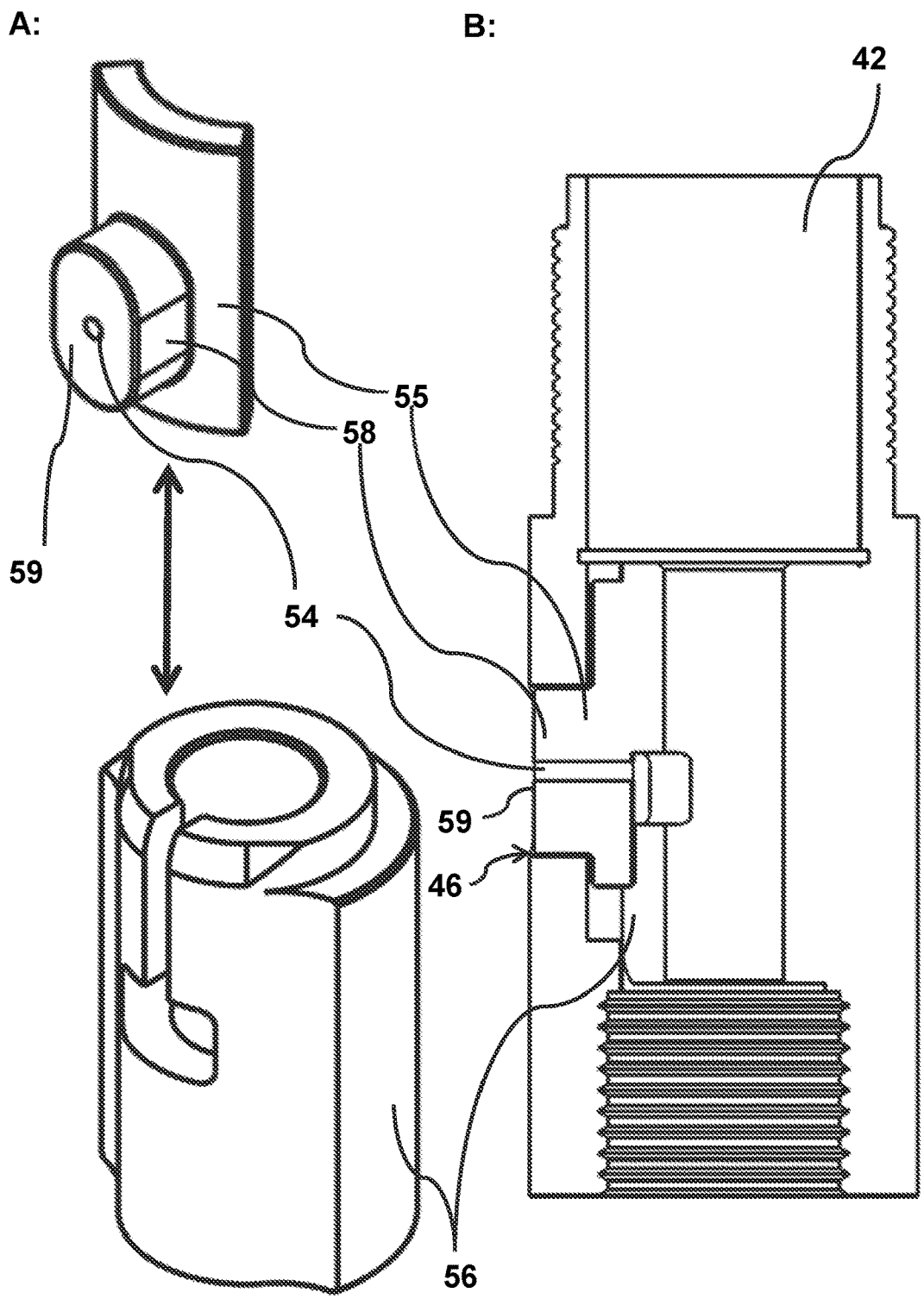
FIG. 10 illustrates an oxidation-reduction electrode (A) and cross-section of a probe body having an oxidation-reduction electrode (B)

FIG. 10 illustrates an oxidation-reduction electrode 54 (A) and cross-section of a probe body 42 having an oxidation-reduction electrode (B).

The oxidation-reduction electrode 54 comprises an electrode body 55. The electrode body 55 encapsulates the metal electrode. The electrode body 55 comprises a protrusion 58 complementary to a through going recess 46 in the probe body 42, see FIG. 10B. The protrusion 58 has an outer face 59 with an exposed part of the metal electrode.

The reference line for the oxidation-reduction electrode 54 points to the metal electrode.

The oxidation-reduction electrode 54 has a curved part adapted for engaging with the cylindrical shape of the probe body 42.

The protrusion 58 has an extent such that the outer face 59 and probe body 42 form a flush surface.

The electrode body 55 has a back side (not shown) which is to engage with an oxidation-reduction electrode holder.

The oxidation-reduction electrode holder 56 has a substantially cylindrical shape with a slit towards a central recess, where the slit and central recess are adapted for engaging the oxidation-reduction electrode 54 when the oxidation-reduction electrode 54 and the oxidation-reduction electrode holder is positioned inside the probe body 42 as seen in FIG. 10B. The entire connection is very sturdy, such that the oxidation-reduction electrode 54 can experience large forces or pressures without drifting and thereby either reducing the resolution, or in worse case, corrupting the data completely.

Figure 11:
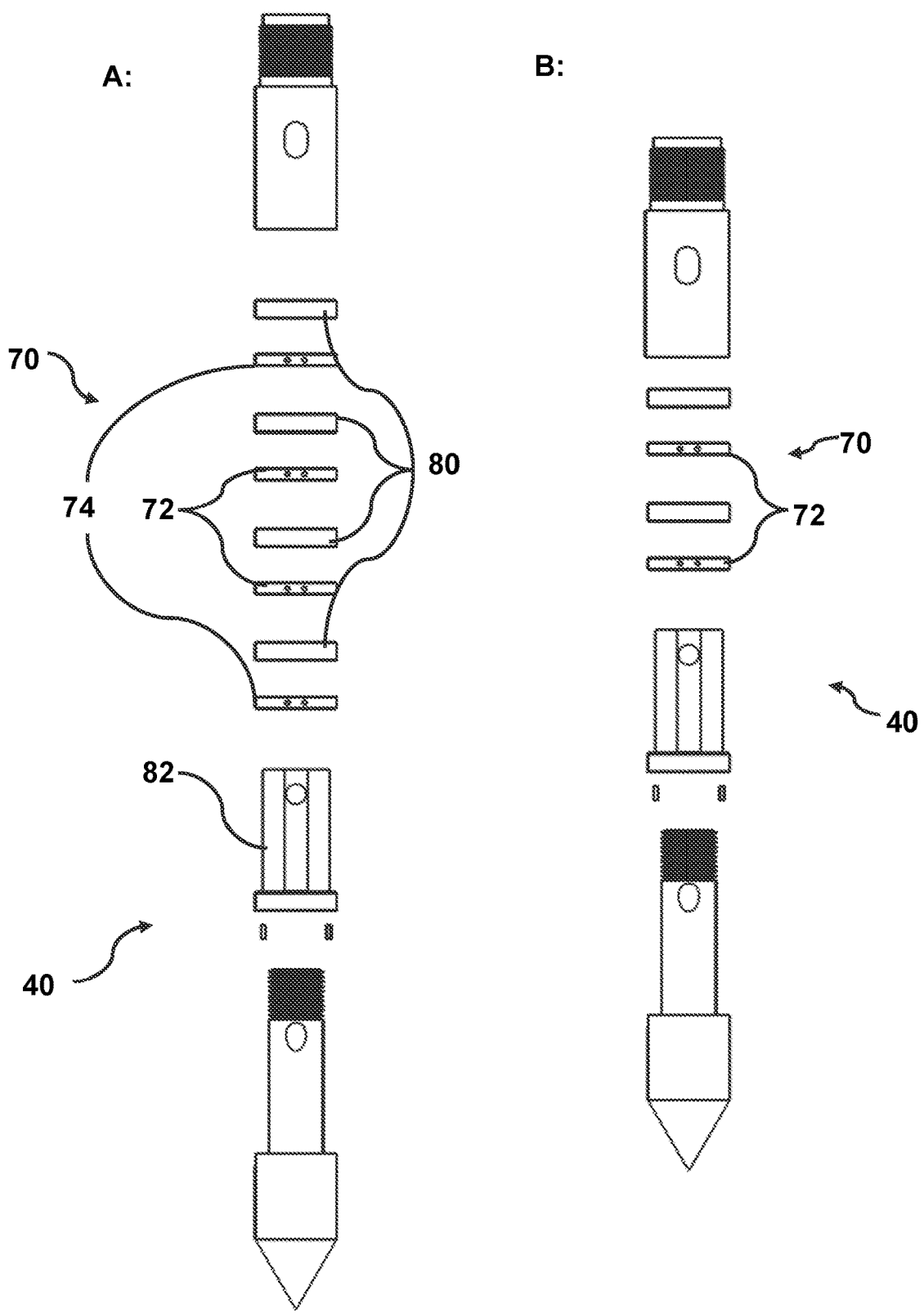
FIG. 11 illustrates a probe having a meter with four electrodes (A) and a probe having a meter with two resistivity electrodes (B)

FIG. 11A illustrates a probe 40 having a meter 70 with four electrodes 72, 74 (A). The two resistivity electrodes 72 and the two current electrodes 74 are all ring electrodes and positioned in a Wenner configuration.

The electrodes 72, 74 are to be isolated from the rest of the probe 40 by plastic rings 80 positioned between the electrodes 72, 74 and a plastic tube 82.

FIG. 11B illustrates a probe 40 having two resistivity electrodes 72. In this case current electrodes 74 (not shown) are to be placed at a surface 12 of a formation 10.

The resistivity electrodes 72 are ring electrodes.

The resistivity electrodes 72 are to be isolated from the rest of the probe 40 by plastic rings 80 positioned between the electrodes 72 and a plastic tube 82.

Figure 12:
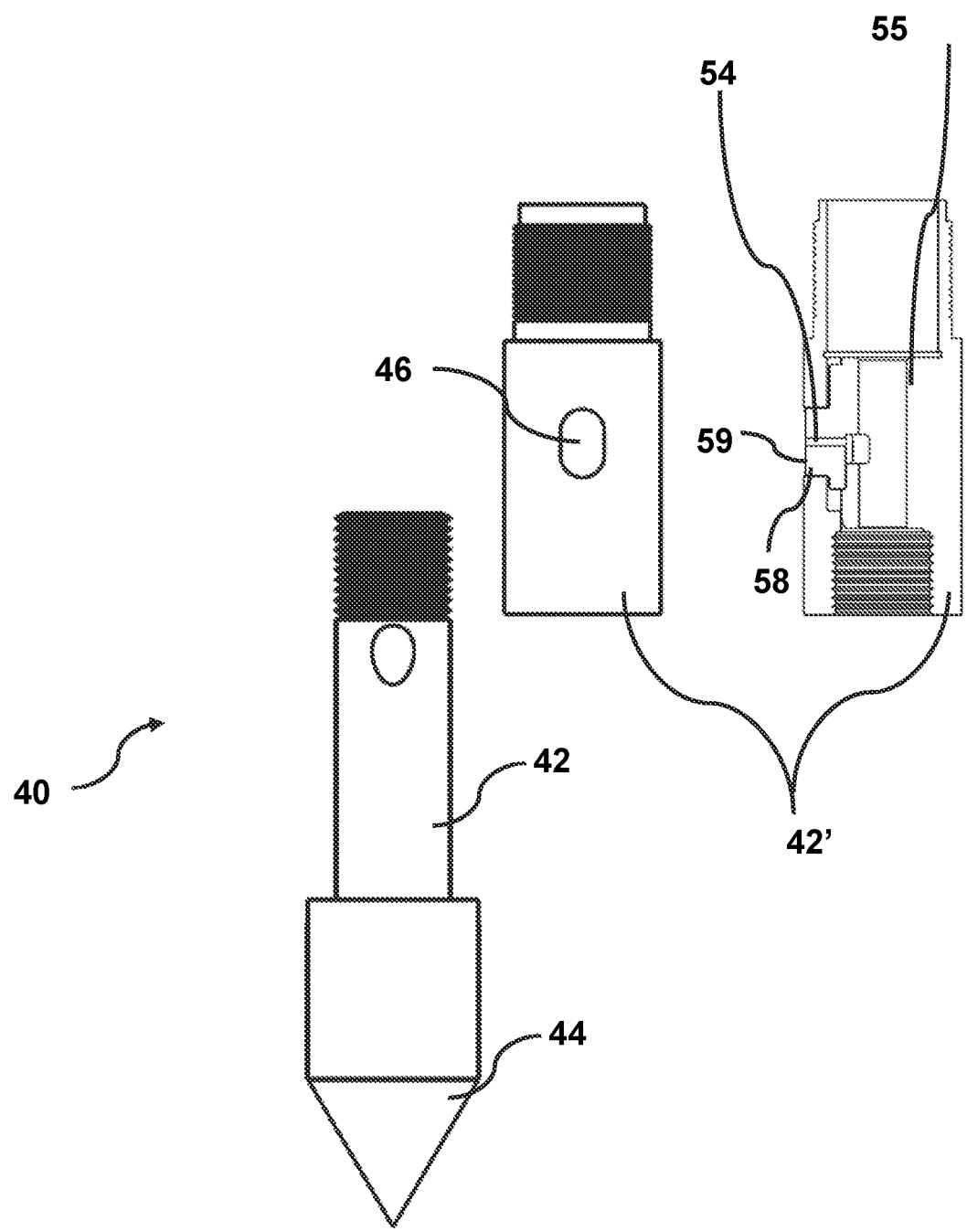
FIG. 12 illustrates a probe with an oxidation-reduction electrode.

FIG. 12 illustrates probe 40 with an oxidation-reduction electrode 54.

The probe 40 has a probe body 42 with a probe front 44. Where the probe front 44 has a pointed end for easing the penetration. The probe 40 has another probe body 42' with an oxidation-reduction electrode 54 to be connected to the probe body 42 with the probe front 44.

The oxidation-reduction electrode 54 comprises an electrode body 55. The electrode body 55 encapsulates the metal electrode. The electrode body 55 comprises a protrusion 58 complementary to a through going recess 46 in the probe body 42. The protrusion 58 has an outer face 59 with an exposed part of the metal electrode.

Figure 13:
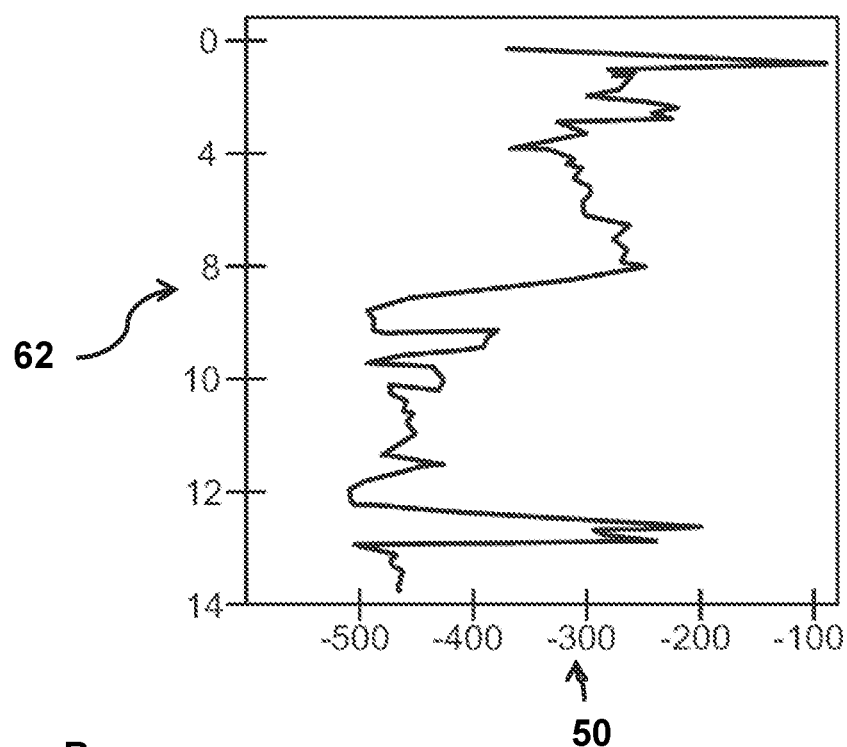
FIG. 13 illustrates an oxidation-reduction potential as a function of penetration and a resistivity measurement as a function of penetration.
Figure 13:
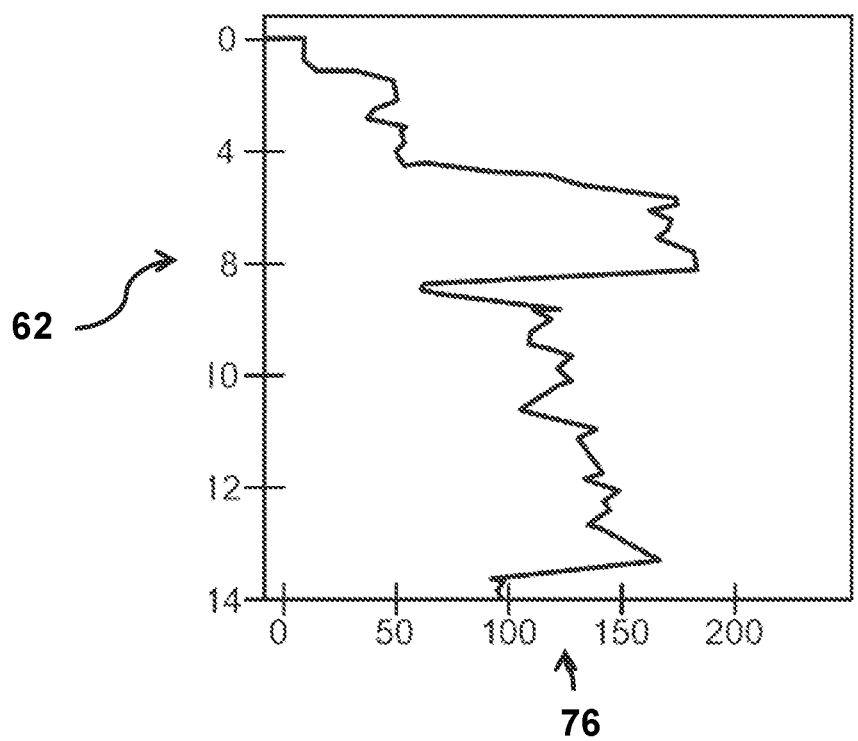

FIG. 13 illustrates an oxidation-reduction potential 50 as a function of penetration 62 (A) and a resistivity 76 measurement as a function of penetration 62 (B).

FIG. 13A discloses a graph of a formation 10, which is reduced as the measured oxidation-reduction potential 50 at all penetrations 62 is negative, thus, this formation supports or could support bacteria capable of denitrification.

FIG. 13B discloses a graph of a formation 10, which has been studied using Direct current. The resistivity 76 measurement is plotted as function of the penetration 62. The lithography of the formation 10 can be determined from the resistivity 76. Since water-bearing layers such as sand have different oxidation-reduction potentials 50 compared to non-water-bearing layers, the lithography of the formation 10 is important when interpreting any oxidation-reduction potential surveys.

The invention claimed is:

1. A method of determining an oxidation-reduction potential in a formation having a surface, the method including the following steps:
    placing a reference electrode at the surface;
    penetrating by direct push drilling a probe carrying an oxidation-reduction electrode into the formation, while the reference electrode is at the surface;
    determining the oxidation-reduction potential as a potential difference between the reference electrode and the oxidation-reduction electrode, wherein the step of determining is performed during the penetrating step.

2. The method according to claim 1, wherein the act of penetrating is performed by directing the probe as a function of time.

3. The method (1000) according to claim 1, wherein the act of penetrating includes establishing a penetration of the probe into the formation; and wherein the act of determining the oxidation-reduction potential is performed as a function of the penetration.

4. The method (1000) according to claim 1, further including the steps of retracting the probe from the formation and performing a direct current resistivity measurement during retraction.

5. The method according to claim 1, further including the steps of:
using a meter of the probe to measure a direct current resistivity, and
determining resistivity as a function of time, penetration, or both time and penetration.

6. A system for determining in situ oxidation-reduction potential in a formation having a surface separating the formation from an ambient atmosphere, the system (20) comprising:
a probe including a probe body and an oxidation-reduction electrode, the probe configured and arranged to penetrate into the formation;
a reference electrode external to the probe configured and arranged for placement on the surface of the formation; and
a controller configured and arranged to
communicate with the probe and the reference electrode;
determine the oxidation-reduction potential as a potential difference between the reference electrode and the oxidation-reduction electrode;
wherein the oxidation-reduction electrode is a metal electrode substantially encapsulated in and galvanically isolated from the probe body, and the oxidation-reduction electrode includes an electrode body encapsulating the metal electrode,
wherein the electrode body includes a protrusion and the probe body includes a throughgoing recess in the probe body, and the protrusion is complementary to the throughgoing recess, the protrusion has an outer face with an exposed part of the metal electrode.

7. The system according to claim 6, further including
a penetrometer communicatively coupled with the controller, the controller further configured and arranged to determine the oxidation-reduction potential as a function of the probe penetration into the formation.

8. The system according to claim 6, further including a timer communicatively coupled with the controller, the controller further configured to determine the oxidation-reduction potential as a function of time.

9. The system according to claim 6, wherein the probe further includes a meter configured and arranged for measuring a direct current resistivity, and the controller is further configured and arranged to determine resistivity as a function of time, penetration, or both time and penetration.

10. The system according to claim 6 to perform the method of determining the oxidation-reduction potential according to claim 1.

11. A computer-readable medium having stored thereon the computer program of claim 10.

12. The system according to claim 6, wherein the probe is further configured and arranged to retract out of the formation and while the probe is retracting the controller circuitry is further configured and arranged to perform a direct current resistivity measurement.

13. The system according to claim 6, wherein the probe further includes a meter configured and arranged for measuring a direct current resistivity.

14. A probe for a penetration into a formation, the probe comprising:
a probe body including a probe front configured and arranged for penetrating the formation, and a throughgoing recess,
an oxidation-reduction electrode, supported by the probe body, and
an electrode body including a protrusion complementary to the throughgoing recess in the probe body, the protrusion having an outer face with an exposed part of the oxidation-reduction electrode,
wherein the oxidation-reduction electrode is a metal electrode, substantially encapsulated in and galvanically isolated from the probe body by the electrode body.

15. Use of the probe according to claim 14 for determining an oxidation-reduction potential in a formation having a surface.

16. The probe of claim 14, wherein the probe further includes a meter configured and arranged for measuring a direct current resistivity.

17. The probe of claim 14, wherein the probe is further configured and arranged to retract out of the formation and perform a direct current resistivity measurement during retraction.

* * * * *